(12) United States Patent
Cardon et al.

(10) Patent No.: US 10,575,958 B2
(45) Date of Patent: Mar. 3, 2020

(54) AUGMENT INSERT, SHOULDER PROSTHESIS AND KIT COMPRISING THE AUGMENT INSERT

(71) Applicant: Tornier, Montbonnot-Saint-Martin (FR)

(72) Inventors: Jean-Emmanuel Cardon, Domene (FR); Benjamin Dassonville, Saint Hilaire du Touvet (FR)

(73) Assignee: Tornier, Montbonnot-Saint-Martin (FR)

( * ) Notice: Subject to any disclaimer, the term of this patent is extended or adjusted under 35 U.S.C. 154(b) by 38 days.

(21) Appl. No.: 15/981,508

(22) Filed: May 16, 2018

(65) Prior Publication Data

US 2018/0333268 A1 Nov. 22, 2018

(30) Foreign Application Priority Data

May 19, 2017 (EP) .................................... 17305587

(51) Int. Cl.
*A61F 2/40* (2006.01)
*A61F 2/30* (2006.01)

(52) U.S. Cl.
CPC ........ *A61F 2/4081* (2013.01); *A61F 2/30734* (2013.01); *A61F 2002/30406* (2013.01); *A61F 2002/30561* (2013.01); *A61F 2002/30607* (2013.01); *A61F 2002/30736* (2013.01); *A61F 2002/4085* (2013.01)

(58) Field of Classification Search
CPC ................ A61F 2/4081; A61F 2/30734; A61F 2002/30406; A61F 2002/30561
See application file for complete search history.

(56) References Cited

U.S. PATENT DOCUMENTS

| | | |
|---|---|---|
| 9,241,801 B1 | 2/2016 | Parry et al. |
| 2006/0069444 A1 | 3/2006 | Deffenbaugh |
| 2010/0161066 A1 | 6/2010 | Iannotti et al. |
| 2016/0045323 A1 | 2/2016 | Kovacs et al. |

FOREIGN PATENT DOCUMENTS

WO WO 2011/156504 12/2011

OTHER PUBLICATIONS

European Search Report issued in EP Application No. 17305587, dated Oct. 26, 2017, in 1 page.
International Search Report and Written Opinion issued in PCT Application No. PCT/EP2018/063170, dated Jul. 30, 2018, in 15 pages.

*Primary Examiner* — Jason-Dennis N Stewart
(74) *Attorney, Agent, or Firm* — Knobbe Martens Olson & Bear, LLP

(57) ABSTRACT

This augment insert (200), comprises a coupling member (204) for securing the augment insert to a glenoid component (103) of a shoulder prosthesis (101), and a body (202), comprising a first side (206), configured to bear against a scapular side (107) of the glenoid component when the augment insert is secured to the glenoid component by means of the coupling member; and a second side, opposed to the first side and configured to bear against or be adjacent to a scapula of a patient. According to the invention, the body (202) comprises at least one breakable portion (230), extending from the first side (206) to the second side and configured to be broken off the body. The aperture (234) is provided for accommodating an engaging member (111) of the glenoid component (103), said engaging member protruding from a scapular surface (127) of the scapular side (107) of the glenoid component (103) and being configured for securing the shoulder prosthesis to the scapula.

15 Claims, 14 Drawing Sheets

AUGMENT INSERT, SHOULDER PROSTHESIS AND KIT COMPRISING THE AUGMENT INSERT

The invention concerns an augment insert, a shoulder prosthesis comprising such an augment insert, a kit comprising such an augment insert and a method of using such an augment insert.

The invention relates to the domain of shoulder arthroplasty, preferably for a human patient, alternatively for an animal patient.

A natural shoulder joint comprises a glenoid cavity of concave shape, formed on a scapula of the patient and a humeral head of convex shape, formed at an end of the humerus of the patient. Arthrosis or the like, implying a worn shoulder joint, may require replacement of the shoulder joint of a patient by a shoulder prosthesis through surgery.

Known shoulder prosthesis comprise a glenoid component, configured to be implanted in the glenoid cavity, and a humeral component, configured to be implanted at the humeral head.

Anatomic shoulder prosthesis are known, characterized by a glenoid component of concave shape, cooperating with a humeral component of convex shape, alike a natural shoulder joint. Generally, the glenoid component of anatomic shoulder prosthesis requires few implantation means, typically only one stem, for implantation in the scapula of the patient. For example, this stem is of porous structure for osseous colonization, which is sufficient for fixing and maintaining the glenoid component.

Reverse shoulder prosthesis are also known, characterized by a glenoid component of convex shape, cooperating with a humeral component of concave shape, contrary to a natural shoulder joint. Due to the geometrical configuration of the reverse shoulder prosthesis, including shifted rotation center, the mechanical stress exerted onto the glenoid component is more important than for the anatomic shoulder prosthesis. Thus, it is usually required to provide stronger implantation means, typically several screws, for a reliable fixation of the glenoid component to the scapula of the patient.

Reverse and anatomic shoulder prosthesis may be adapted respectively to different cases specific to the patient.

In some particular cases, the wear does not regularly affect the patient's glenoid cavity, but is rather centered on superior and/or posterior side thereof. To the contrary, some cases display a more distributed wear of the glenoid cavity. Thus, it is often required to adapt the shape of the glenoid component to the shape of the worn glenoid cavity of the patient.

This may be done by adding cement of bone graft for compensating the shape differences of the glenoid component relative to the patient's bone. However, in some cases, cement or bone graft are not thick enough or do not allow correct and reliable integration of the glenoid component to the patient's bone.

This may also be done by providing glenoid components of different shapes, optionally in combination with cement or bone graft. However, providing many glenoid components of different types raise economic and practical problems. In particular, insofar as for a given patient, the surgeon needs to choose the reversed or anatomic glenoid implant which is the most suitable to the patient in terms of size and geometry, glenoid components of various size and geometry need to be available to the surgeon, which induces substantial inventory constraints.

US 2016/0045323 A1 discloses modular reverse and anatomic shoulder glenoid components that may be provided with an augment insert for modifying the shape of part of the component in contact with the scapular bone.

However, most of the anatomic and reverse glenoid components differ in that stems or screws are distributed at different locations at their scapular side, or due to a different shape of scapular surface. Consequently, two different sets of augment inserts are usually provided, each adapted respectively to the anatomic and to the reverse glenoid components.

One of the goals of the present invention is to overcome at least some of the aforementioned problems, especially the constraints related to inventories of the various pieces used to provide a modular shoulder prosthesis.

To this end, the invention concerns:
An augment insert, comprising:
  a coupling member for securing the augment insert to a glenoid component of a shoulder prosthesis, and
  a body, comprising:
    a first side, configured to bear against a scapular side of the glenoid component when the augment insert is secured to the glenoid component by means of the coupling member;
    a second side, opposed to the first side and configured to bear against or be adjacent to a scapula of a patient; and
    at least one breakable portion, extending from the first side to the second side and configured to be broken off the body,
  wherein when the breakable portion is broken off the body, an aperture is opened through the body, said aperture extending from the first side to the second side.

Thanks to the invention, the breakable portion may be broken off or not, depending if the augment insert should be secured to a glenoid component with a scapular side of a first shape or with a scapular side of a second shape, different from the first shape. Thus, a single augment insert is suitable for two different types of glenoid components. More specifically, a single augment insert may be adapted in situ to the shape of the glenoid component to be secured to, by choosing whether to break off the breakable portion. Thereby, the number of available augment inserts in inventory can be reduced. In particular, when the augment insert is to be secured to a glenoid component of which scapular side comprises a specific engaging member, the aperture may provide free space for accommodating this engaging member. Thus, said engaging member may extend through the aperture of the augment insert, when the augment insert is secured to such a glenoid component.

Further advantageous and optional features of the invention are defined below:
  the aperture is provided for accommodating an engaging member of the glenoid component, said engaging member protruding from a scapular surface of the scapular side of the glenoid component and being configured for securing the shoulder prosthesis to the scapula;
  the body comprises a pre-cut outline, the pre-cut outline delimiting the breakable portion, and forming an aperture edge of the aperture when the breakable portion is broken off the body;
  the body comprises a peripheral edge delimiting the first side and the second side, the peripheral edge comprises a thinner radial edge portion and a thicker labrum edge portion, and the breakable portion is provided at the radial edge portion;

the augment insert is at least partially made of a material with a lattice structure;

the augment insert is made from additive manufacturing;

the first side is of smoother surface and the second side is of rougher surface.

The invention also concerns:

A shoulder prosthesis, comprising:

an augment insert as defined above, and a glenoid component, comprising a scapular side to which the augment insert is secured by the coupling member of the augment insert.

Further advantageous and optional features of the invention are defined below:

the glenoid component comprises an articular side opposed to the scapular side, the articular side having a convex articular surface;

the glenoid component comprises an articular side opposed to the scapular side, the articular side having a concave articular surface.

The invention also concerns:

A kit, comprising:

a first glenoid component, comprising a scapular side, a second glenoid component, comprising a scapular side which is shaped differently from the scapular side of the first glenoid component, an augment insert as defined below, the augment insert being:

shape-compatible for bearing against the scapular side of the first glenoid component and shape-incompatible for bearing against the scapular side of the second glenoid component, when the breakable portion is not broken off the body, and shape-compatible for bearing against the scapular side of the second glenoid component, when the breakable portion is broken off the body.

Further advantageous and optional features of the invention are defined below:

the breakable portion has a surface, which extends at the first side of the body when the breakable portion is not broken off, and which is shaped to match a scapular surface of the scapular side of the first glenoid component when the first side bears against said scapular side, and when the breakable portion is broken off the body, an aperture is opened through the body, said aperture extending from the first side to the second side, the aperture being positioned for accommodating a first engaging member of the scapular side of the second glenoid component;

the scapular side of the first glenoid component comprises a second engaging member, the scapular side of the second glenoid component comprises a third engaging member, the coupling member of the augment insert is configured for securing indifferently: the second engaging member, when the first side bears against the scapular side of the first glenoid component, and the third engaging member, when the first side bears against the scapular side of the second glenoid component.

the scapular side of the first glenoid component comprises a fourth engaging member, the scapular side of the second glenoid component comprises a fifth engaging member, and the body being provided with a first through-opening or first cut-away portion for accommodating the fourth engaging member when the first side bears against the scapular side of the first glenoid component and a second through-opening or second cut-away portion for accommodating the fifth engaging member when the first side bears against the scapular side of the second glenoid component.

the first glenoid component comprises an articular side opposed to the scapular side and comprising a convex articular surface, and the second glenoid component comprises an articular side opposed to the scapular side and comprising a concave articular surface.

The invention also concerns: A method of using the augment insert according to claim 1, for forming a shoulder prosthesis, the method comprising the following steps:

Step A): choosing if the augment insert should be secured to:

choice A1): a first glenoid component comprising a first scapular side, or choice A2): a second glenoid component comprising a second scapular side;

if choice A1) is chosen at Step A):

Step B1): not breaking off the breakable portion, and

Step C1): securing the augment insert to the first scapular side of the first glenoid component by means of the coupling member of the augment insert, for obtaining that the shoulder prosthesis comprises the first glenoid component and the augment insert, secured to the first scapular side of the first glenoid component by the coupling member of the augment insert;

if choice A2) is chosen during at Step A):

Step B2): breaking off the breakable portion, and

Step C2): securing the augment insert to the second scapular side of the second glenoid component by means of the coupling member of the augment insert, for obtaining that the shoulder prosthesis, comprises the second glenoid component and the augment insert, secured to the second scapular side of the second glenoid component by the coupling member of the augment insert.

Further advantageous and optional features of the invention are defined below:

According to an embodiment, steps A), as well as steps B1) and C1) or B2) and C2) are performed in-situ by a surgeon or one of his assistants, for example in an operating room of a medical facility.

Step A) is performed depending on the specific medical case of the patient, in particular of the specific shoulder pathology of the patient.

Steps A), B1) and C1), or steps A), B2) and C2), are performed before the surgeon performs a step D) of implanting the shoulder prosthesis in the patient.

Step D) includes implanting the prosthesis in the patient, by securing said prosthesis to the scapula of the patient. In a preferred embodiment, engaging members of the prosthesis are engaged into the scapula of the patient for securing the prosthesis to the scapula of the patient. When the prosthesis is implanted in the patient, the augment insert is interposed between the scapula of the patient and the glenoid component of the prosthesis. When the prosthesis is implanted in the patient, the second side of the augment insert bears against the scapula of the patient or is at least adjacent thereto. Preferably, when the prosthesis is implanted in the patient a part of the scapular side bears against the scapula of the patient.

Since the augment insert is secured to the glenoid component before step D), the risk of separating or misplacing the augment insert is reduced.

Steps A), as well as steps B1) and C1) or B2) and C2) may be performed before or after the surgeon performs a step E) of opening the patient.

If choice A1) is chosen at step A), and optionally if steps B1) and C1) have already been performed, the surgeon may afterwards prefer choice A2), and perform the following steps:

Step F): separating the augment insert from the first glenoid component,

Step B2), and

Step C2).

The method also comprises a step G) of closing the patient, for example by stitching up, after step D) is performed.

According to another embodiment, one or all the steps A), B1), C1), B2) and C2) may be performed by a person unqualified for surgery. For example, these steps may be performed for preparing several prosthesis of different type in advance, for a later surgical usage by one or more surgeons. The choice of which prosthesis is to be used for a specific patient is then made by said surgeon.

Preferably, the person unqualified for surgery belongs to personnel in charge of the inventory of a medical facility, in particular a facility where the surgeon is intended to implement the prosthesis in the patient.

Alternatively, the person unqualified for surgery belongs to personnel in charge of the manufacturing or the assembling of the prosthesis, in a manufacturing facility or factory separate from the abovementioned medical facility.

The invention is explained through illustrative and non-limitative examples described below and illustrated by the annexed figures where:

Figure 1:
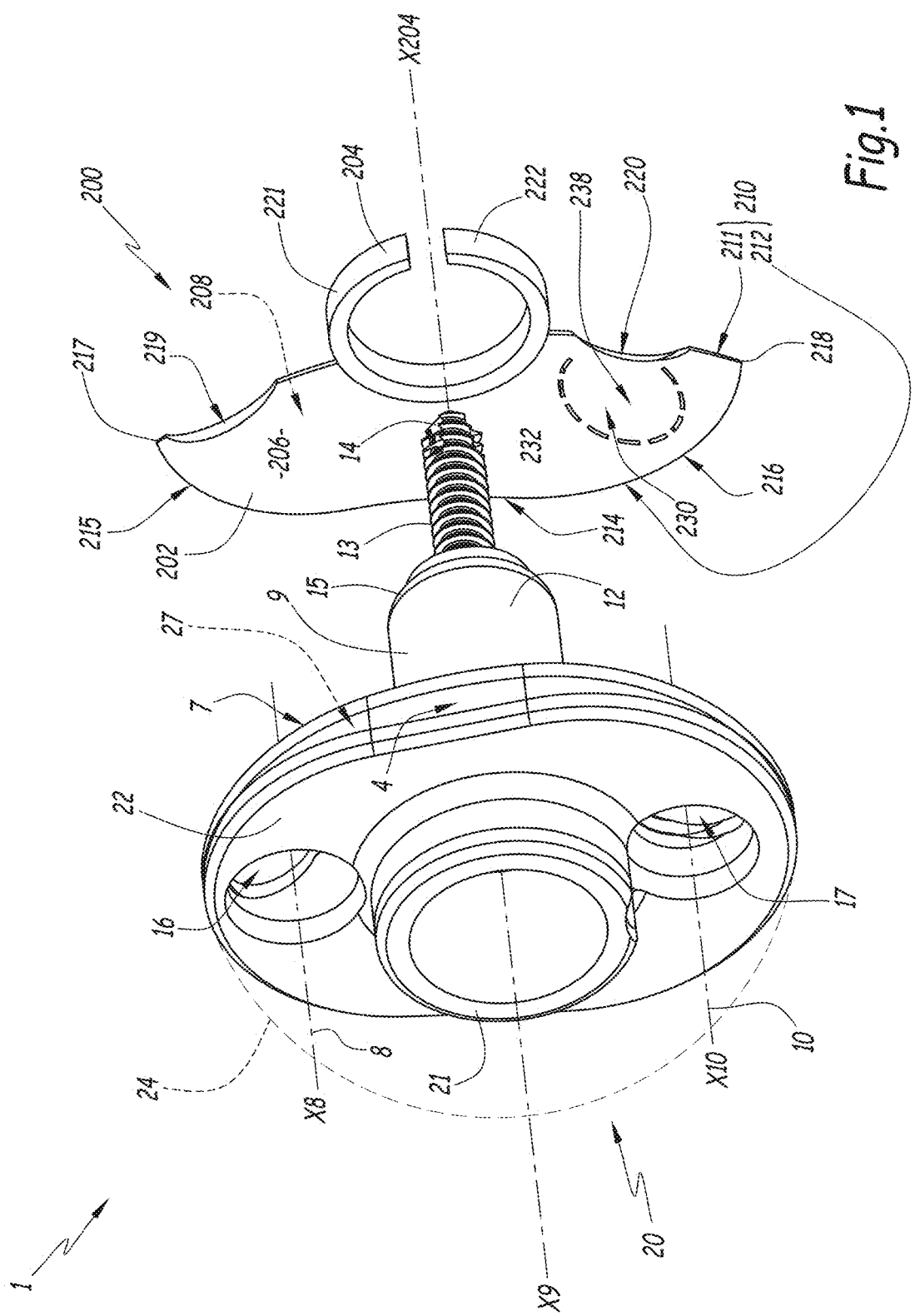
FIGS. 1 and 2 are exploded perspective views of a shoulder prosthesis according a first embodiment of the invention.

Referring to FIGS. 1 to 5, a shoulder prosthesis 1 is shown in. Referring to FIGS. 6 to 10, a shoulder prosthesis 101 is shown in. The shoulder prosthesis 1 and 101 include an augment insert 200, illustrated alone on FIG. 11. The same augment insert 200 is used for both shoulder prosthesis 1 and 101. The shoulder prosthesis 1 and 101 respectively include a glenoid component 3 and a glenoid component 103, which are different from each other, as described below.

Figure 5:
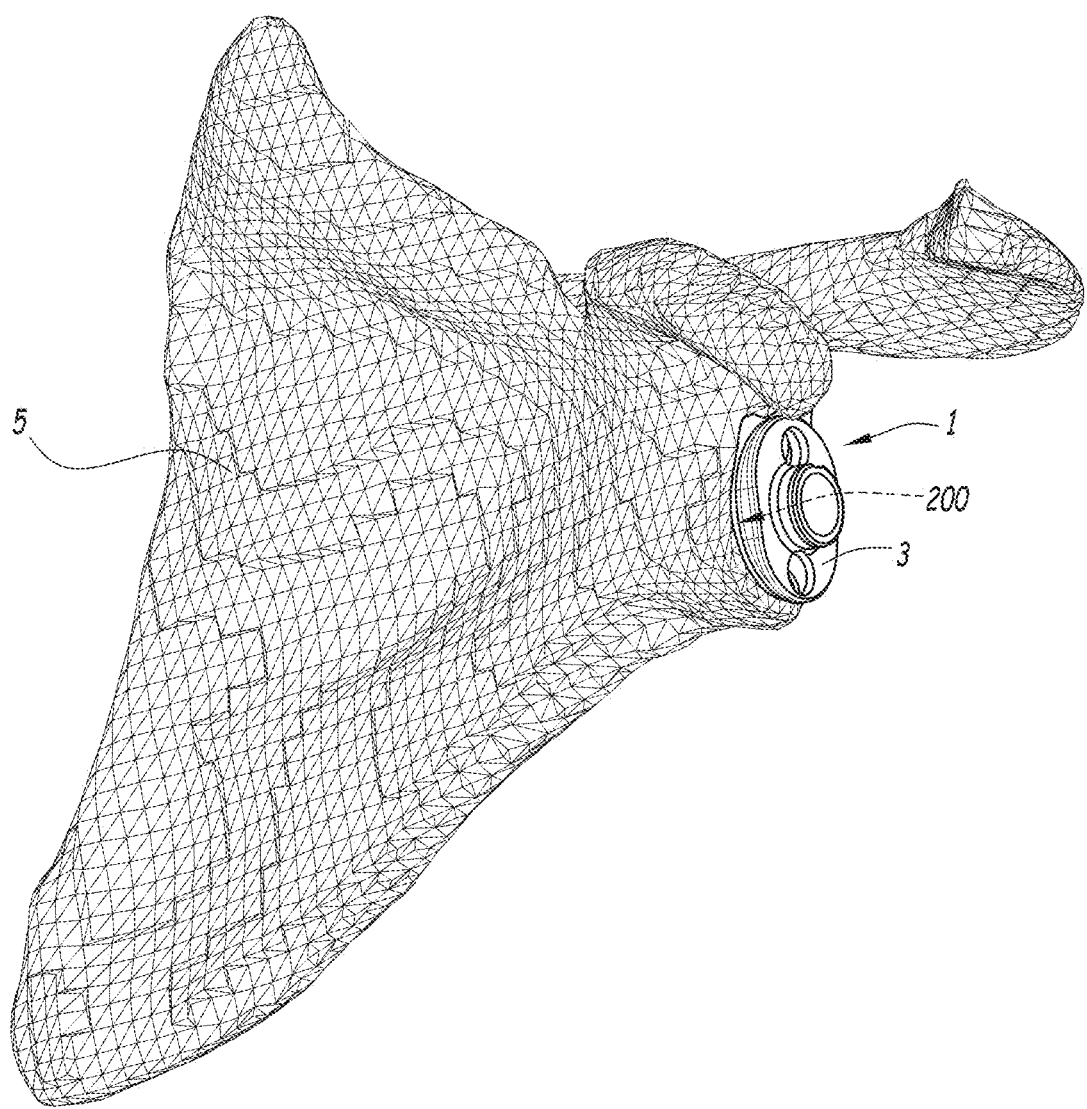
FIG. 5 is a perspective view of the shoulder prosthesis of FIGS. 1 to 4, mounted onto a scapula of a patient.
Figure 10:
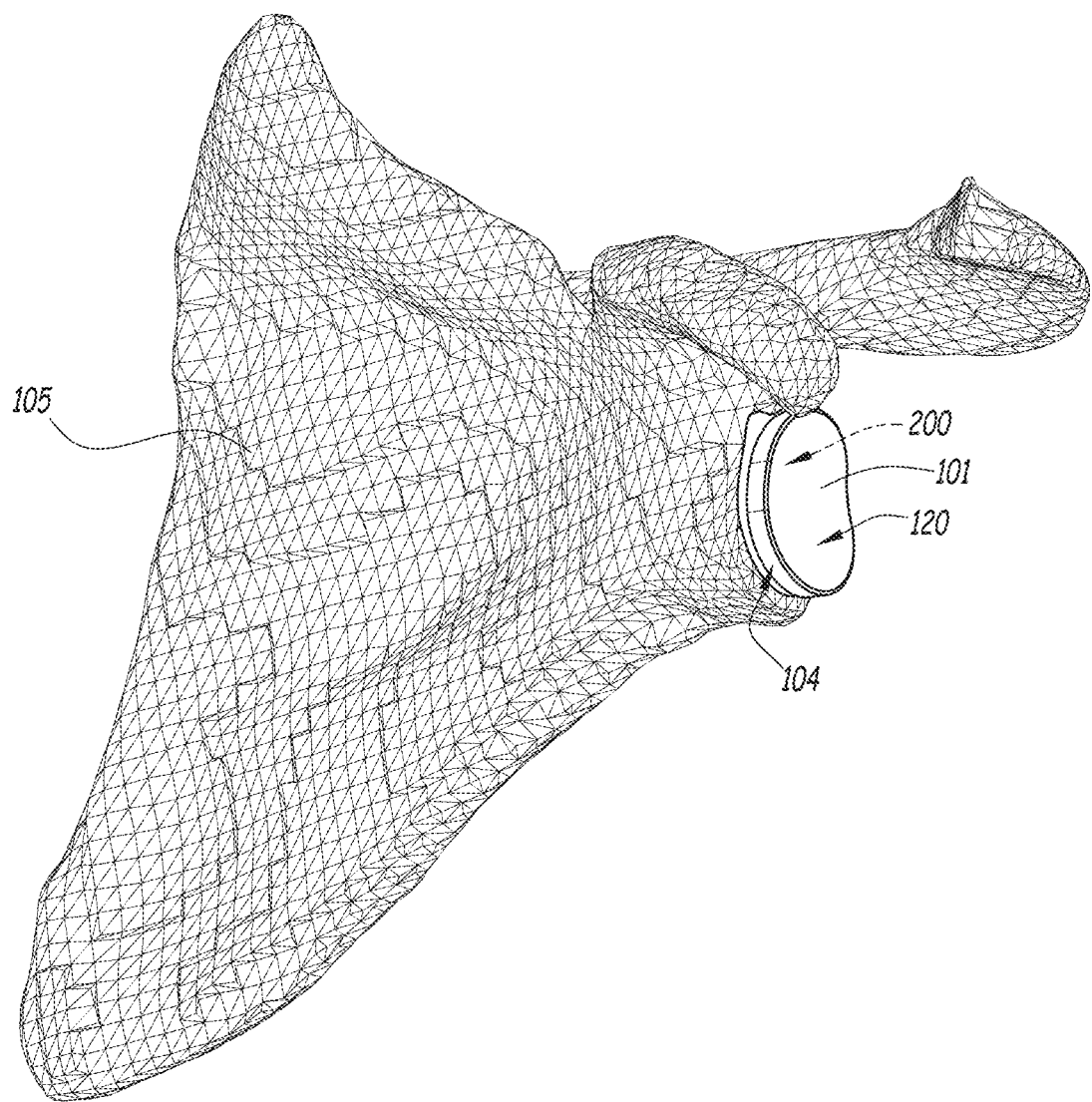
FIG. 10 is a perspective view of the shoulder prosthesis of FIGS. 6 to 9, mounted onto a scapula of a patient.
Figure 11:
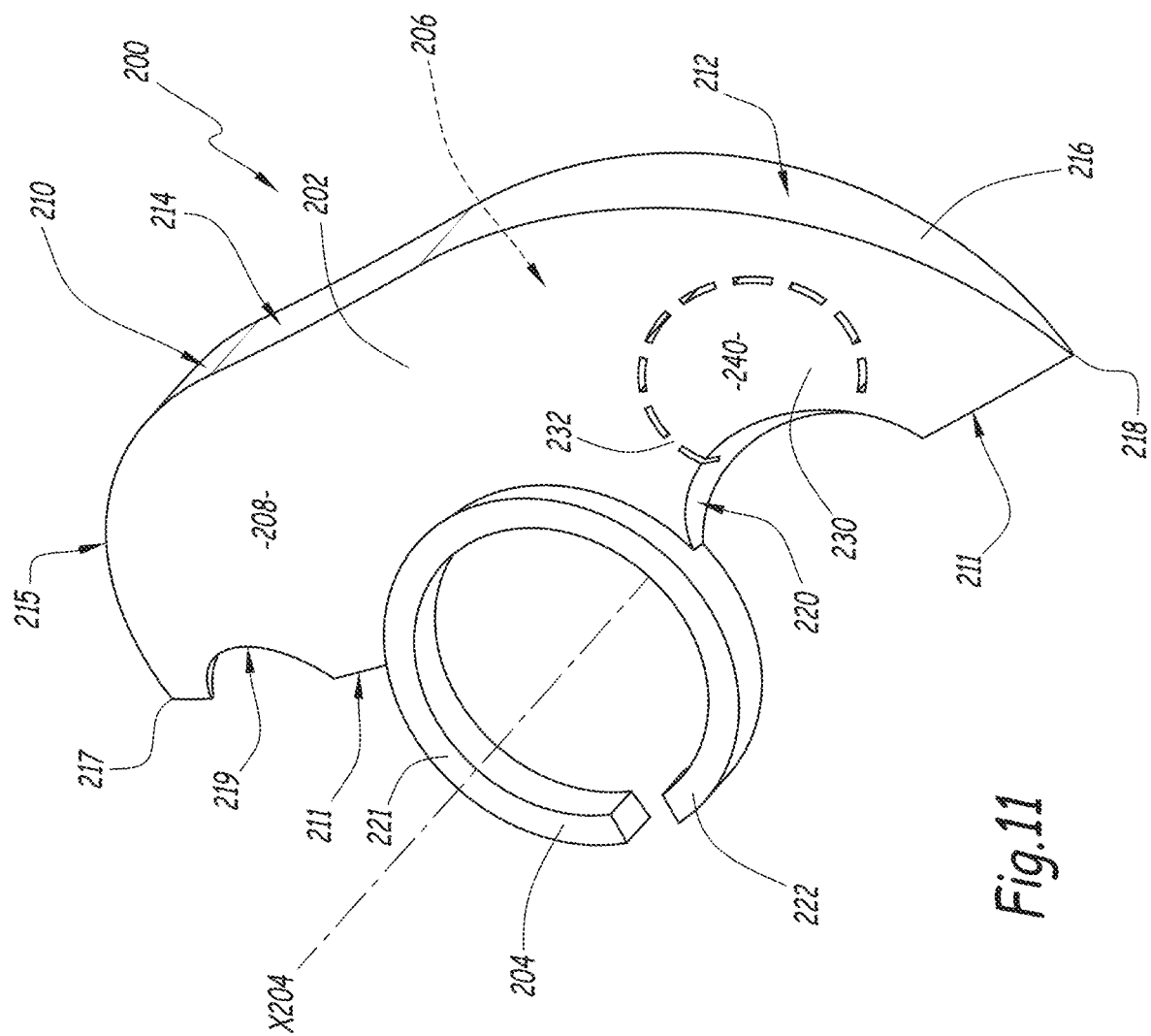
FIG. 11 is a perspective view of an augment insert belonging to both shoulder prosthesis of FIGS. 1 to 10.

As shown respectively on FIGS. 5 and 10, both shoulder prosthesis 1 and 101 are configured for being implanted respectively in a scapula 5 and a scapula 105 of human patients, at the glenoid cavity thereof. In both cases, the augment insert 200 is introduced between the concerned glenoid component 3 or 103 and the concerned scapula 5 or 105, for adapting to the patient specific shape of the scapula 5 and 105. Depending on the shape of the scapula of the patient, an augment insert of different shape and/or thickness than the augment insert 200, may be chosen to adapt or compensate for said shape. The augment insert 200 is used as a leveling spacer of predetermined thickness, for modular adaptation of the shape of the shoulder prosthesis 1 or 101 specifically a patient's scapula.

The shoulder prosthesis 1 and 101 illustrated on FIGS. 1 to 11 are configured for a left shoulder. Symmetrical features may be applied for a right shoulder.

As shown on FIGS. 1 to 11, the augment insert 200, mainly comprises a body 202, having the abovementioned levelling function, and a coupling member 204, for securing the augment insert 200 to one of the glenoid components 3 and 103.

The body 202 comprises two opposed sides 206 and 208, each comprising a slightly curved surface. Alternatively, one or both sides 206 and 208 define a flat surface. In the present example, each side 206 and 208 is generally shaped as a crescent, so that the augment insert 200 covers only a portion of the glenoid cavity of the patient, corresponding to approximately a half of the glenoid cavity.

When the augment insert 200 is secured onto the glenoid component 3 or 103, the side 206 bears against a scapular side 7 or a scapular side 107 of the concerned glenoid component 3 or 103. The side 206 may match or mirror the geometry of the scapular sides 7 and 107 as explained below.

When the prosthesis 1 or 101 is implemented in the patient, the side 208 bears against or is adjacent to the glenoid cavity of the scapula 5 or 105. The augment insert 200 is chosen so that the geometry of the side 208 substantially matches or mirrors the geometry of the glenoid cavity of the scapula 5 or 105. Optionally, the side 208 can be made patient specific, which means that the side 208 can be manufactured specifically for a predetermined patient, based on the geometry or features specific to this patient. In brief, a scan such as computed tomography (CT) or magnetic resonance imaging (MRI) is performed of a specific patient anatomy, and a portion of the implant, such as side 208, is shaped specifically to accommodate the patient's anatomy.

The aforementioned "shape and/or thickness" of the augment insert 200 is defined by geometrical features of the sides 206 and 208. Augment inserts of different shape and/or thickness than the illustrated augment insert 200 include for example a different distance or length between the sides 206 and 208 and/or a different relative inclination and/or a different geometry of one or both sides 206 and 208.

The body 202 also comprises a peripheral edge 210 delimiting and linking both sides 206 and 208. The edge 210 is defined all around the body 202 and connects sides 206 and 208. The peripheral edge 210 defines a surface oriented approximately perpendicularly to the sides 206 and 208.

Figure 4:
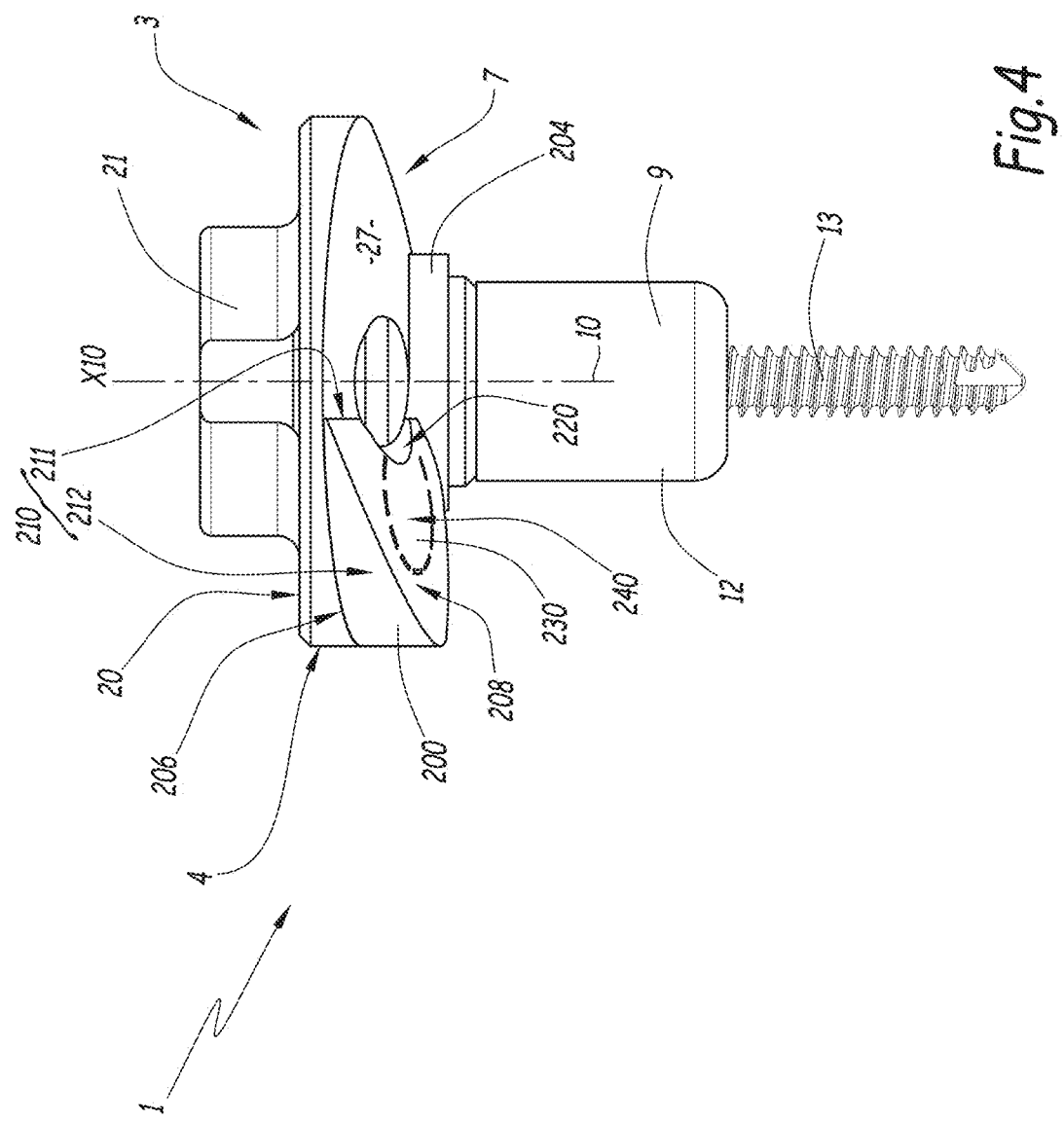
FIG. 4 is a side view of the shoulder prosthesis of FIGS. 1 to 3.

As best visible on FIG. 4, preferably, the side 206 is inclined relative to the side 208. In other words, side 206 is not parallel to side 208, so that the body 202 is shaped as a wedge.

The edge 210 comprises a radial edge portion 211 and a labrum edge portion 212 opposed to each other. The radial portion 211 is thinner than the labrum portion 212. The thickness of the portions 211 and 212 is to be measured from side 206 to side 208. The side 206 and the side 208 form an angle originating from the radial edge portion 211

The labrum edge portion 212 is intended to be extending along a portion of the glenoid labrum (i.e. the peripheral rim of the glenoid cavity) of the scapula 5 or 105 of the patient when the shoulder prosthesis 1 or 101 is implemented. As best visible on FIG. 1, the labrum edge portion 212 comprises a substantially flat median surface 214 and two extremal surfaces 215 and 216 extending therefrom, the two surfaces 215 and 216 being strongly curved towards a similar direction.

The radial edge portion 211 is intended to extend across the glenoid cavity of the scapula 5 or 105 of the patient when the shoulder prosthesis 1 or 101 is implemented. In other words, the edge portion 211 may extend along a diameter or a chord of the labrum, along the concave surface of the glenoid cavity. The radial edge portion 211 is slightly curved for corresponding to the concave shape of the glenoid cavity. The portion 211 extends substantially parallel to the median surface 214 of the body 202. The radial edge portion 211 links the surface 215 to the surface 216 of the labrum edge portion 212. The radial edge portion 211 and the labrum edge portion 212 meet at two opposed corners 217 and 218 of the edge 210.

As a summary, in the illustrated example, the edge 210 comprises the radial edge portion 211 and the labrum edge portion 212. The radial edge portion 211 and the labrum edge portion 212 are connected at the corners 217 and 218. The labrum edge portion 212 comprises three surfaces 215, 214 and 216, linking corner 217 to corner 218. The detail III of FIG. 3 illustrates only the edge 210 along with its features as described above.

Turning to the glenoid component 3 depicted on FIGS. 1 to 5, it may be seen that said glenoid component 3 comprises a main body 22, including the abovementioned scapular side 7 and an opposed articular side 20.

Figure 2:
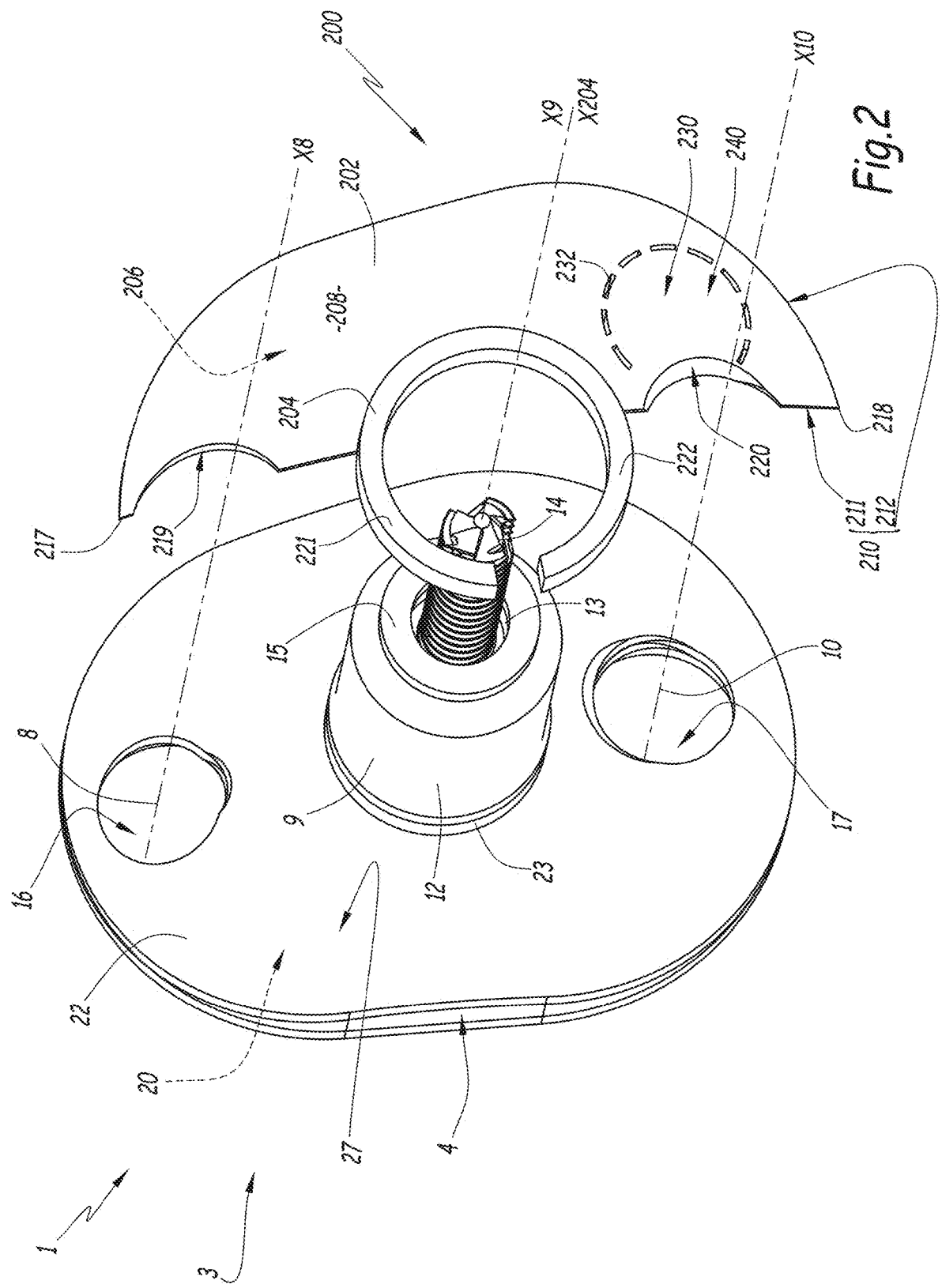
Figure 3:
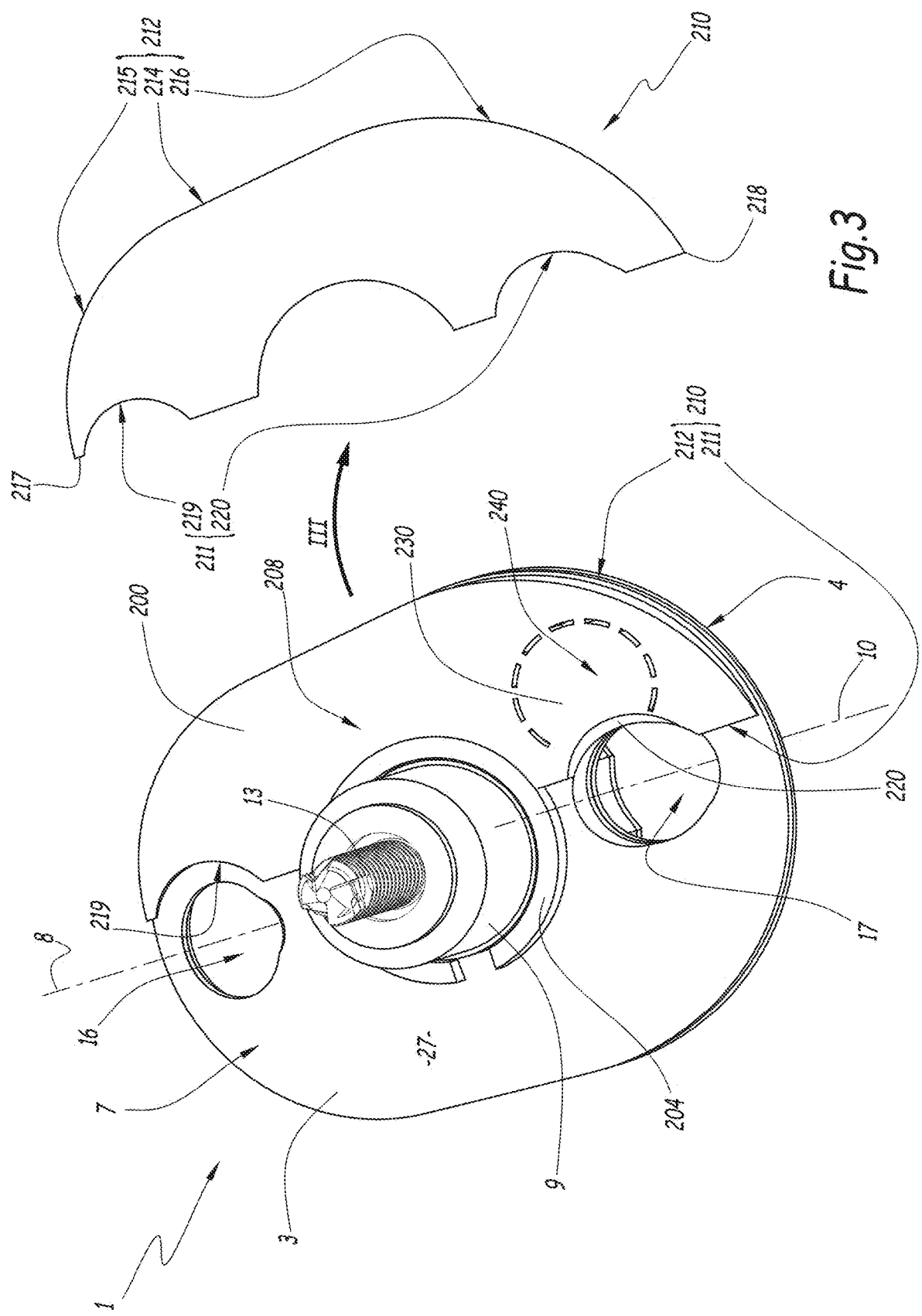
FIG. 3 is an assembled perspective view of the shoulder prosthesis of FIGS. 1 and 2.

As visible on FIGS. 2 and 3, the scapular side 7 comprises a slightly curved scapular surface 27, which shape or geometry corresponds to the side 206 of the augment insert 200. This allows the side 206 of the augment insert 200 to bear against side 7. More specifically, the surface of side 206 is designed to be completely, or at least partially, in contact with the scapular surface 27, when the augment insert is secured to the glenoid component. Scapular surface 27 is partially covered by surface 206. The bone contact is shared between scapular surface 27 and augment insert surface 202.

The scapular side 7 of the glenoid component 3 has a peripheral edge 4 delimiting the scapular surface 27 of the side 7. As visible on FIGS. 3 and 4, the labrum edge portion 212 and a portion of the edge 4 are put in correspondence when the insert 200 is secured to the glenoid component 3. In other words, the labrum edge portion 212 matches with the edge 4 along a portion thereof. More visibly on FIG. 4, the respective peripheral surfaces of the labrum edge portion 212 and of the edge 4 are arranged continuously when the insert 200 is secured to the glenoid component 3.

More generally, the peripheral edge 4 has a generally elliptical shape corresponding to the shape of the rim of the glenoid cavity of the scapula 5 of the patient.

When the augment insert 200 is secured to the glenoid component 3, only a portion of the scapular surface 27 is covered by said augment insert 200. Thus, a portion of the surface 27 remains uncovered and may bear against glenoid cavity of the scapula 5 of the patient, when the shoulder prosthesis 1 is implemented in the patient. In the present example, the portion of the scapular side 7 covered by the augment insert 200 is a posterior portion of the scapular side 7, while the anterior portion is left uncovered. Thus, a posterior levelling correction is applied. In other words, the augment insert 200 corrects the orientation of the glenoid component 3, by interposing between the glenoid component 3 and the glenoid cavity of the scapula 5 at a posterior area thereof. Alternatively, the augment insert 200 may be configured so that another portion of the scapular side 7 is covered, such as an upper portion, for applying an upper levelling correction. In this case, the augment insert 200 corrects the orientation of the glenoid component 3, by interposing between the glenoid component 3 and the glenoid cavity of the scapula 5 at an upper area thereof. Alternatively, the body 202 may be shaped for covering the entire scapular surface 27. The correction to be applied depends on the shape of the glenoid cavity onto which the shoulder prosthesis 1 is to be implanted.

Preferably, the side 206 is of smoother surface and the side 208 is of rougher surface. This rougher surface may be obtained by coating, sand blasting, hydroxyapatite (HAP) deposit, formation of a macro structure, or any other method depending on the application. Thus, when the prosthesis 1 or 101 is implemented, the rougher surface of the side 208 promotes osseous colonization or adhesion of the side 208 by the patient's bone. The side 206 having a smoother surface, it is less prompt to wearing the side 7 or 107 of the respective glenoid component 3 or 103 in contact.

More generally, the body 202 is configured to resist compressive stress exerted on the side 206 by the chosen glenoid component 3 or 103 and on the side 208 by the scapula 5 or 105 of the patient.

Preferably, at least the body 202 of the augment insert 200 is of lattice structure. By "lattice structure", it is understood that the body 202 is made of a material with a porous geometry configured for promoting osseous colonization and/or body fluid impregnation. Alternatively, the entire augment insert 200 may be made of such material. Alternatively, only a part of the augment insert 200 may be made of such material, including at least one of the sides 206 or 208. A non-porous geometry may be chosen for all or a part of the body 202, instead of the abovementioned lattice structure, depending on the application.

The augment insert may be made of a metal, such as titanium, or any other metal depending on the application. Another suitable material may be chosen instead of metal, depending on the application, for example a ceramic material or a thermoplastic material such as Polyethylene (PET) or polyetheretherketone (PEEK). Alternately, a ceramic such as pyrocarbon may be employed. Any other suitable material may be used depending on the case.

Preferably, at least the body 202 of the augment insert 200 is made from additive manufacturing, preferably direct metal laser sintering. This allows in particular making the side 208 patient specific. More preferably, the entire augment insert 200 is made from additive manufacturing. Alternatively, manufacturing the augment insert 200 includes a step of molding or connecting at least the body 202, or the body 202 and the coupling member 204.

Preferably, the coupling member 204 is integral with the body 202. Alternatively, the coupling member 204 may be a separate part from the body 202, which are permanently assembled together during manufacturing of the augment insert 200, or at a later stage.

As visible on FIGS. 2 to 4, the scapular side 7 of the glenoid component 3 comprises three engaging members 8, 9 and 10, protruding from the scapular surface 27. On the figures, the two engaging members 8 and 10 are respectively illustrated symbolically by two axis lines, whereas the engaging member 9 is illustrated realistically.

By "engaging member", it is understood any suitable member for securing a shoulder prosthesis to the scapular bone of the patient. Depending on the application, an engaging member may include a screw, a stem, an anchor or the like.

The engaging member 9 is protruding from a central location of the surface 27. A central location of the member 9 on side 7 is preferred, for a better stability of the implantation of the glenoid component 3.

In the present example, said member 9 comprises a frustoconical tubular body 12 protruding from the surface 27 along an axis X9, generally orthogonal to the surface 27. The body 12 has a base 23 and a free end 15 coaxial with the axis X9. The body 12 is connected to the surface 27 by the base 23. The end 15 is distant from the surface 27. The base 23 is of larger diameter or size than the free end 15. The tubular body 12 and/or the surface 27 may be porous for osseous colonization thereof, for securing the prosthesis 1 to the scapula 5.

Preferably, the glenoid component 3 also comprises a tubular body 21 protruding from the articular side 20, coaxially and opposite to the body 12.

In the present example, the engaging member 9 comprises a screw 13, configured for engaging the scapula 5. This screw 13 is inserted through the main body 22, from side 20 to side 7. For the present example, the screw 13 is introduced through the tubular body 21. The screw 13 is further introduced coaxially through the tubular body 12, so that a sharp end 14 of the screw 13 protrudes from a free end 15 of the tubular body 12. A head of the screw 13, not visible on the figures, opposite to the sharp end 14, lays inside the tubular body 21. The prosthesis 1 may be secured to the scapula 5 by engagement of the screw into the scapula 5.

Depending on the application, tubular body 21 may be omitted. In this case, if the abovementioned screw 13 is provided, it is inserted through the tubular body 12 from the surface of side 22.

Depending on the application, the engaging member 9 may comprise only one among the screw 13 and the tubular body 12.

Any other suitable engaging member 9 may be chosen instead of the engaging member 9 described above, depending on the application.

The coupling member 204 of the augment insert 200 is configured for securing to the engaging member 9 at the scapular side 7 of the glenoid component 3. For this purpose, the coupling member 204 is provided at the radial edge portion 211. More precisely, the coupling member 204 is provided at a median location of the radial edge portion 211. Thus the augment insert 200 is secured to the glenoid component 3 at a central location of side 7, so that the fixation is especially stable.

Alternatively, the coupling member 204 may be provided at another location of the edge 210 of the augment insert 200, for securing the augment insert 200 to an engaging member of the glenoid component 3 which is located at a lateral location of the scapular side thereof. Otherwise, the engaging member 9 can be provided at another location of side 7, the location of the coupling member 204 being modified accordingly. In particular, the coupling member 204 can be provided at a central or lateral location of the side 206 or through the body 202. For any embodiment, the coupling member 204 is attached to the body 202, preferably fixedly.

In the example illustrated on FIGS. 1 to 11, the coupling member 204 comprises a ring coaxial with an axis X204 of the augment insert 200. Said axis X204 is substantially orthogonal, or slightly inclined, relative to the surfaces of sides 206 and 208. Said axis X204 is positioned out of the peripheral edge 210. The ring of the coupling member 204 is configured to be connected to the tubular body 12 for securing the augment insert 200 to the body 12.

In the present example, the ring comprises two resilient arm portions 221 and 222 of circular shape, so that the ring may be snapped onto the body 12. Alternatively, the coupling member 204 comprises a continuous ring that may be snap-fitted onto the body 12. Alternatively, the coupling member 204 comprises a continuous ring that may be tight-fitted or friction fit onto the body 12. The ring of the coupling member 204 may form a frustoconical sleeve for conical fitting onto the frustoconical body 12.

The presence of the coupling member 204 provides a particularly high stability to the augment insert 200 when the prosthesis 1 is implemented in the body of the patient, thereby preventing any relative movement of the augment insert 200 and the glenoid component 3. In addition, it is possible to manipulate the prosthesis 1 while the augment insert 200 is in a configuration secured onto the glenoid component 3, so that the augment insert 200 remains adequately positioned onto the glenoid component 3 during manipulation of the prosthesis 1.

In the illustrated example, most of the body 12 and the screw 13 of the member 9 extends beyond the side 208, by passing through the coupling member 204, as visible on FIGS. 3 and 4. Thus, both body 12 and screw 13 may be used for providing fixation of the prosthesis 1 to the scapula 5.

Turning to the engaging members 8 and 10, said members 8 and 10 are respectively coaxial with an axis X8 and an axis X10 of the glenoid component 3. The axis X8, X9 and X10, as for their respective members 8, 9 and 10, may extend side by side in parallel orientations, or optionally in diverging or converging directions for a more reliable fixation of the prosthesis 1 into the scapula 5. In the present example, the engaging members 8 and 10 are provided at either side of the engaging member 9. In other words, while the engaging member 9 is at a central location of the side 7, the engaging members 8 and 10 are at a lateral location thereof. Preferably, the engaging members 8, 9 and 10 are arranged along a same line of the side 7, preferably a diametric line.

In the present example, the glenoid component 3 comprises two through-holes 16 and 17, coaxial respectively with the axis X8 and X10. The through-holes 16 and 17 are provided through the body 22, from side 20 to side 7. In the present example, the engaging members 8 and 10 both comprise a screw, coaxial respectively with the axis X8 and the axis X10 and accommodated through the holes 16 and 17 respectively. A sharp end of each screw is pointed in a direction similar than the sharp end 14 of the screw 13. Thus, the screws 16 and 17 may engage the scapula 5 of the patient, thereby securing the prosthesis 1 to said scapula 5. Any other suitable embodiment of engaging members 8 and 10 may be provided instead of screws.

In the present example, the augment insert 200 comprises two distinct cut-away portions 219 and 220, for accommodating respectively the engaging members 8 and 10, so that said members 8 and 10 may extend beyond the side 208 of the augment insert 200. In the present example, each cut-away portion 219 and 220 is provided at the radial edge portion 211. The cut-away portions 219 and 220 are located on either side of the coupling member 204. One or both of the cut-away portions 219 and 220 may have an anti-rotation function for the fixation of the augment insert 200 relative to the glenoid component 3 around axis X9, by respective cooperation with one or both of the engaging members 8 and 10. For this purpose, the shape of the cut-away portions 219 and/or 220 may be chosen as corresponding to the shape of their respective member 8 and/or 10. In the present example, each cut-away portion 219 and 220 is of semi-circular or concave shape. In the present example, as visible on FIG. 3, when the augment insert 200 is secured to the glenoid component 3, the concave surface of the cut-away portion 220 is aligned with the circular surface of the through-hole 17 so that the cut-away portion 220 may bear against the engaging member 10.

The same pattern may optionally be applied for cut-away portion 219 and through-hole 16. Preferably, only one of the cut-away portions 219 and 220 bears against a lateral engaging member of the glenoid component 3.

Depending on the number and the location of the engaging members provided at the covered part of the scapular side of the glenoid component 3, less or more cut-away cut-away portions may be provided for accommodating said engaging members. Also, through-openings of similar function may be provided from side 206 to side 208, inside the peripheral edge 210, depending on the number and location of engaging members of the glenoid component.

Instead of two lateral engaging members 8 and 10, no lateral engaging member, one lateral engaging member or more lateral engaging members may be provided on the scapular side of the glenoid component 3. Through-openings or cut-away portions may be provided on the augment insert 200 accordingly.

For any embodiment considered, it is preferred at least one of the engaging members 8, 9 and/or 10 extends beyond side 208, of the augment insert 200 when the augment insert 200 is secured to the glenoid component 3. It can be provided that only one of the engaging members extends beyond side 208. Thus, the concerned engaging member can be engaged into the scapula 5 for fixation of the prosthesis 1.

In the present example, the body 22 comprises of two parts made of a different material, a scapular part extending from the scapular side 7 and an articular part extending from the articular side 20. The scapular part and articular part are fixed to each other at a medial plane of the body 22 located between the sides 7 and 22, substantially perpendicular to the axis X9. For example, the articular part is metallic, while the scapular part is made of a thermoplastic such as polyethylene. In an embodiment, the scapular part may have a lattice structure while the articular part has a solid structure. In the present example, the tubular body 12 has an outer surface, for engaging the scapula 5, which is integral with the scapular part. In the present example, the tubular body 12 has an inner surface which is integral with the articular part. Alternatively, the tubular body 12 may be integral with one part or the other or both. In the present example, the tubular body 21 is integral with the articular part, although it may be integral with the scapular part or both parts.

Alternatively, the body 22 may be made of a single integral part of one material.

As illustrated in dashed line on FIG. 1, the glenoid component 3 may comprise a glenosphere 24 fixed to the articular side 20. The glenosphere 24 is omitted from the FIGS. 2 to 5. For example, the glenosphere 24 is fixed to the body 22 by means of the engaging members 8 and 10. Alternatively, the glenosphere 24 is fixed to the tubular body 21. For this purpose, the tubular body 21 may be provided with an outer or inner thread for screwing the glenosphere 24 onto the tubular body 21. The glenosphere 24 forms a convex articular component with a convex articular surface. By "convex", it is meant a protruding surface, preferably of spherical shape, configured for cooperating with a non-illustrated corresponding concave articular surface. By "concave", it is meant that the surface is in the shape of a socket, preferably spherical. The glenosphere 24 is configured to cooperate with a concave articular surface provided at a humeral head of the patient in relation with the scapula 5. Said concave articular surface is preferably provided on an artificial humeral head belonging to the prosthesis 1. The concave and the convex articular surfaces together form the artificial joint for the patient, around which the humerus of the patient and the scapula 5 are articulated. The glenoid component 3 having such a glenosphere 24, the prosthesis 1 and the glenoid component 3 may be qualified of "reverse".

The geometric center of the glenosphere 24 is preferably centered on the axis X9.

Instead of being a separate part fixed onto the body 22, the glenosphere 24 may be integral with the body 22.

Any other suitable convex articular component than the glenosphere 24 may be implemented for the glenoid component 3. Instead of a convex articular component, a concave articular component including a concave articular surface may be implemented for the glenoid component 3, for articulation with a convex humeral head. In this case, the glenoid component 3 and the prosthesis may be qualified of "anatomic".

Turning to FIGS. 5 to 10, the prosthesis 101 comprises the glenoid component 103 and the same augment insert 200 as described above.

The glenoid component 103 comprises a main body 122, including the abovementioned scapular side 107 and an opposed articular side 120.

Figure 7:
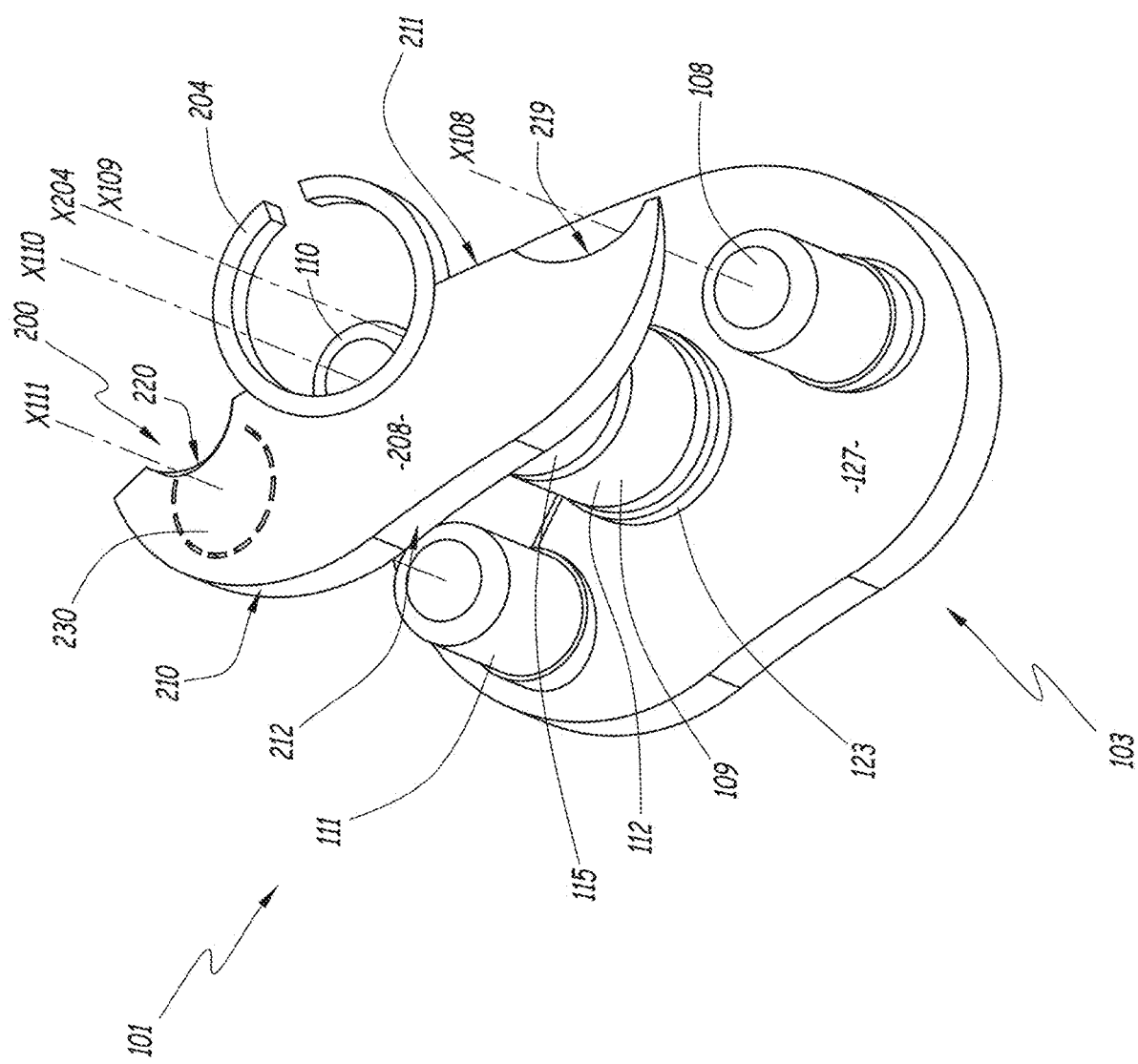

As visible on FIG. 7, the scapular side 107 comprises a slightly curved scapular surface 127, which shape or geometry corresponds to the side 206 of the augment insert 200. Also, the surface 127 is preferably of similar shape than the surface 27 of the scapular side 7 of the glenoid component 3. More specifically, the surface 127 is designed to be completely, or at least in majority, in contact with the surface of the side 206, when the augment insert 200 is secured to the glenoid component 3. This enables the side 206 to bear against side 107.

The scapular side 107 of the glenoid component 103 has a peripheral edge 104 delimiting the surface 127. The edge 104 preferably has a similar shape than the edge 4 of the glenoid component 3. As visible on FIGS. 8 and 9, the labrum edge portion 212 and a portion of the edge 104 are put in correspondence when the insert 200 is secured to the glenoid component 3. In other words, the labrum edge portion 212 matches with the edge 104 along a portion thereof. More visibly on FIG. 9, the respective peripheral surfaces of the labrum edge portion 212 and of the edge 104 are arranged continuously when the insert 200 is secured to the glenoid component 103.

More generally, the peripheral edge 104 has a generally elliptic shape corresponding to the shape of the rim of the glenoid cavity of the scapula 105 of the patient.

When the augment insert 200 is secured to the glenoid component 103, only a portion of the surface 127 is covered by said augment insert 200, similarly to the surface 27. Thus, a portion of the surface 127 remains uncovered and may bear against glenoid cavity of the scapula 105 of the patient, when the shoulder prosthesis 101 is implemented in the patient. In the present example, the portion of the scapular side 107 covered by the augment insert 200 is also a posterior portion of the scapular side 107, while the anterior portion is left uncovered. Thus, a posterior levelling correction is applied.

As visible on FIGS. 6 to 10, the scapular side 107 of the glenoid component 103 comprises four engaging members 108, 109, 110 and 111, protruding from the scapular surface 127.

The engaging member 109 is protruding from a central location of the scapular surface 127.

In the present example, said member 109 comprises a stem 112 of essentially cylindrical shape, protruding from the surface 127 along an axis X109. The axis X109 is generally orthogonal to the surface 127. The stem 112 has a base 123 and a free end 115 coaxial with the axis X109. The stem 112 is connected to the surface 127 by the base 123. The end 115 is distant from the surface 127. The stem 112 and/or the surface 127 may be porous for osseous colonization thereof, for securing the prosthesis 101 to the scapula 105. Alternatively, the stem 112 may be provided with wings, fins or any other suitable anchoring element for implantation into the scapula 105. The prosthesis 101 may be secured to the scapula 105 by engagement of the stem 112 into the scapula 5. Preferably, no screw is provided along axis X109 for fixation of the prosthesis 101 into the scapula 105.

Depending on the application, a different type of engaging member(s) may be provided as the engaging member 109. In particular, engaging member 109 may be of the same type than, or may be identical to, the engaging member 9.

The coupling member 204 of the augment insert 200, otherwise configured for securing to the engaging member 9 of the glenoid component 3, is also configured for securing to the engaging member 109 of the glenoid component 103.

For this purpose, the location of the engaging member 109 on the scapular side 107 is preferably similar to the location of the engaging member 9 for the scapular side 7, should this location be central or not.

For this purpose, it is provided in the present example that the outer diameter or dimensions of the stem 112 is adapted for snap-fitting of the arms portions 221 and 222 of the coupling member 204, when the side 206 of the augment insert 200 is brought into contact of the surface 127.

Thus the coupling member 204 may indifferently be secured onto:
the engaging member 9, for fixation of the augment insert 200 to the glenoid component 3, when the side 206 bears against the side 7 of the glenoid component 3, or
the engaging member 109, for fixation of the augment insert 200 to the glenoid component 103, when the side 206 bears against the side 107 of the glenoid component 103.

More specifically, it may be provided that at least a portion of the outer peripheral surface of the engaging member 9 and of the engaging member 109, configured for securing the coupling member 204, has a similar geometry or at least a compatible shape with the coupling member 204.

If a coupling member of different type than the coupling member 204 is chosen, the engaging member 109 may be adapted accordingly, and vice-versa.

Figure 8:
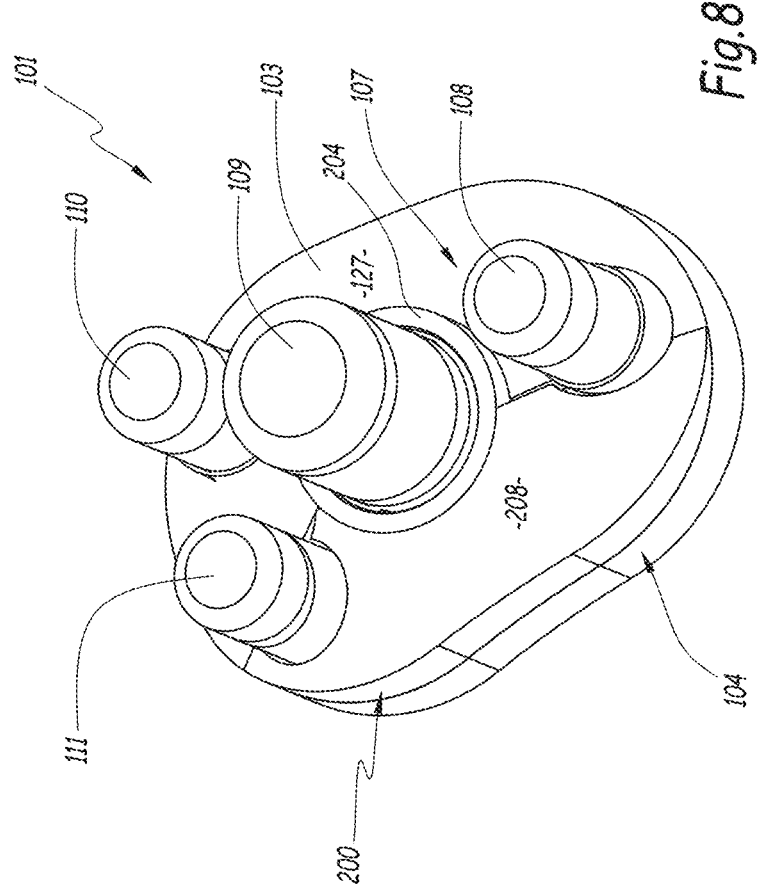
FIG. 8 is an assembled perspective view of the shoulder prosthesis of FIGS. 6 and 7.
Figure 9:
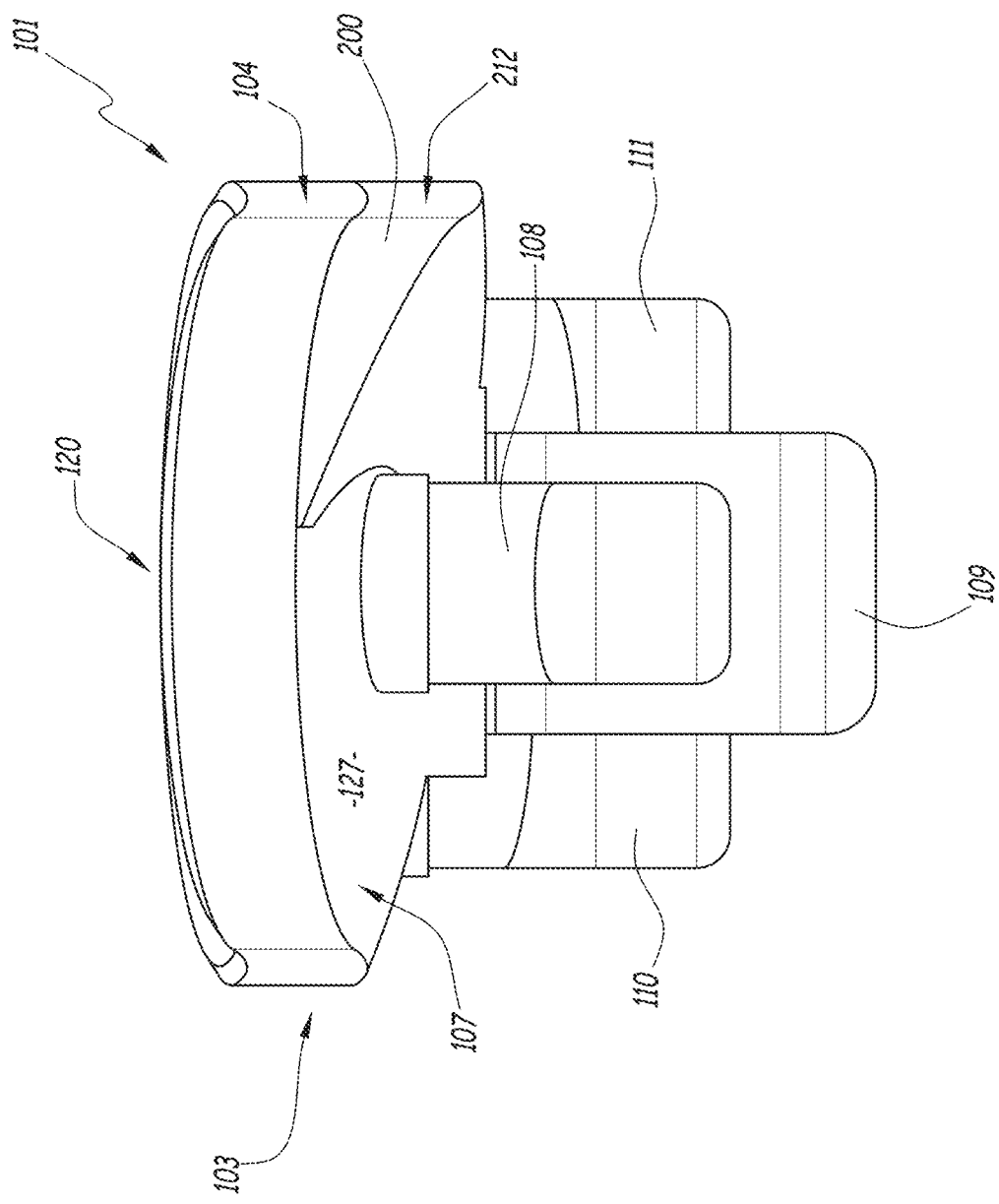
FIG. 9 is a side view of the shoulder prosthesis of FIGS. 6 to 8.

As for member 9, the member 109 is configured to extend beyond the side 208 by passing through the coupling member 204, as visible on FIGS. 8 and 9.

Turning to the engaging members 108, 110 and 111, said members 108, 110 and 111 are respectively coaxial with an axis X108, an axis X110 and an axis X111 of the glenoid component 103. The axis X108, X109, X110 and X111, as for their respective members 108, 109, 110 and 111, may extend side by side in parallel orientations, or optionally in diverging or converging directions for a more reliable fixation of the prosthesis 101 into the scapula 105. In the present example, the engaging members 108, 110 and 111 are distributed around the engaging member 109. In other words, while the engaging member 109 is at a central location of the side 107, the engaging members 108, 110 and 111 are at a lateral location thereof. Preferably, the lateral engaging members 108, 109 and 111 are arranged in a triangle comprising the central engaging member 110.

In the present example, each lateral engaging member 108, 109 and 111 comprises a stem coaxial with the concerned axis X108, X109 or X111, preferably of similar features than the stem 112. The stems of the members 108, 109 and 111 are preferably of smaller diameter and length than the stem 112. Any other suitable embodiment of engaging members 108, 109 and 111 may be provided instead of stems.

One or both of the two cut-away cut-away portions 219 and 220 may be configured for accommodating at least one or more of the lateral engaging members of the glenoid component 103, indifferently from the lateral engaging members of the glenoid component 3.

The engaging member 110 being located at an uncovered part of the side 107, said member 110 extends beyond the side 208 without passing through the augment insert 200. The member 110 extends outside the peripheral edge 210.

One or more further engaging members similiar to member 110 may additionally be provided.

In the present example, the engaging member 108 is accommodated into the cut-away portion 219 while no engaging member is accommodated in the cut-away portion 220, as visible on FIGS. 7 to 9. Thus, one of the cut-away portions 219 and 220 is provided for accommodation of one of the engaging members of the glenoid component 3, while the other is provided for accommodation of one of the engaging members of the glenoid component 103, ensuring that an anti-rotation function is obtained regardless the augment insert 200 being secured to the glenoid component 3 or 103. Only one of the cut-away portions 219 and 220 used at a time when the augment insert 200 is mounted on one of the glenoid components 3 or 103, while the other cut-away portion 219 or 220 is not used.

The glenoid components 3 and 103 respectively have scapular sides 7 and 107 that are shaped differently, since they include respectively engaging members 8, 9 and 10 and engaging members 108, 109, 110 and 111. As defined above, the location, shape and number of engaging members differ for the glenoid components 3 and 103: they constitute differences of shape for the respective scapular sides 7 and 107 of the glenoid components 3 and 103.

In the present example, the sides 7 and 107 are shaped differently although the surfaces 27 and 127 have a similar shape. Alternatively, the surfaces 27 and 127 may also be of different shape, adding to the shape differences of sides 7 and 107. In a non-illustrated embodiment, scapular sides of different shape may be obtained for two glenoid components if the scapular surfaces are of different shape, even if the engaging member are at similar locations and/or are of the same number. Any other material element provided on one of the scapular surfaces may generate a difference of shape of the respective scapular sides. In other words, the shape differences described above correspond to geometry differences of the sides 7 and 107, including scapular surface and engaging members.

These shape differences may make an augment insert shape-compatible with a first glenoid component and at the same time shape-incompatible with a second glenoid component with a scapular side of different shape than the first glenoid component, since the augment insert would match the scapular side of the first glenoid component and not match the scapular side of the second glenoid component. When shape-compatible, the augment insert can be secured to the glenoid component. When shape-incompatible, the augment insert cannot properly be secured to the glenoid component. By "shape-compatible", it is understood that the two pieces have a matching shape and can be assembled. By "shape-incompatible", it is understood that the two pieces do not have a matching shape and cannot be assembled as a consequence of this shape incompatibility.

In the present example, the abovementioned cut-away portions 219 and 220 enable the augment insert 200 to be shape compatible with both glenoid components 3, thanks to the cut-away portion 220, and glenoid component 103, thanks to the cut-away portion 219.

Figure 6:
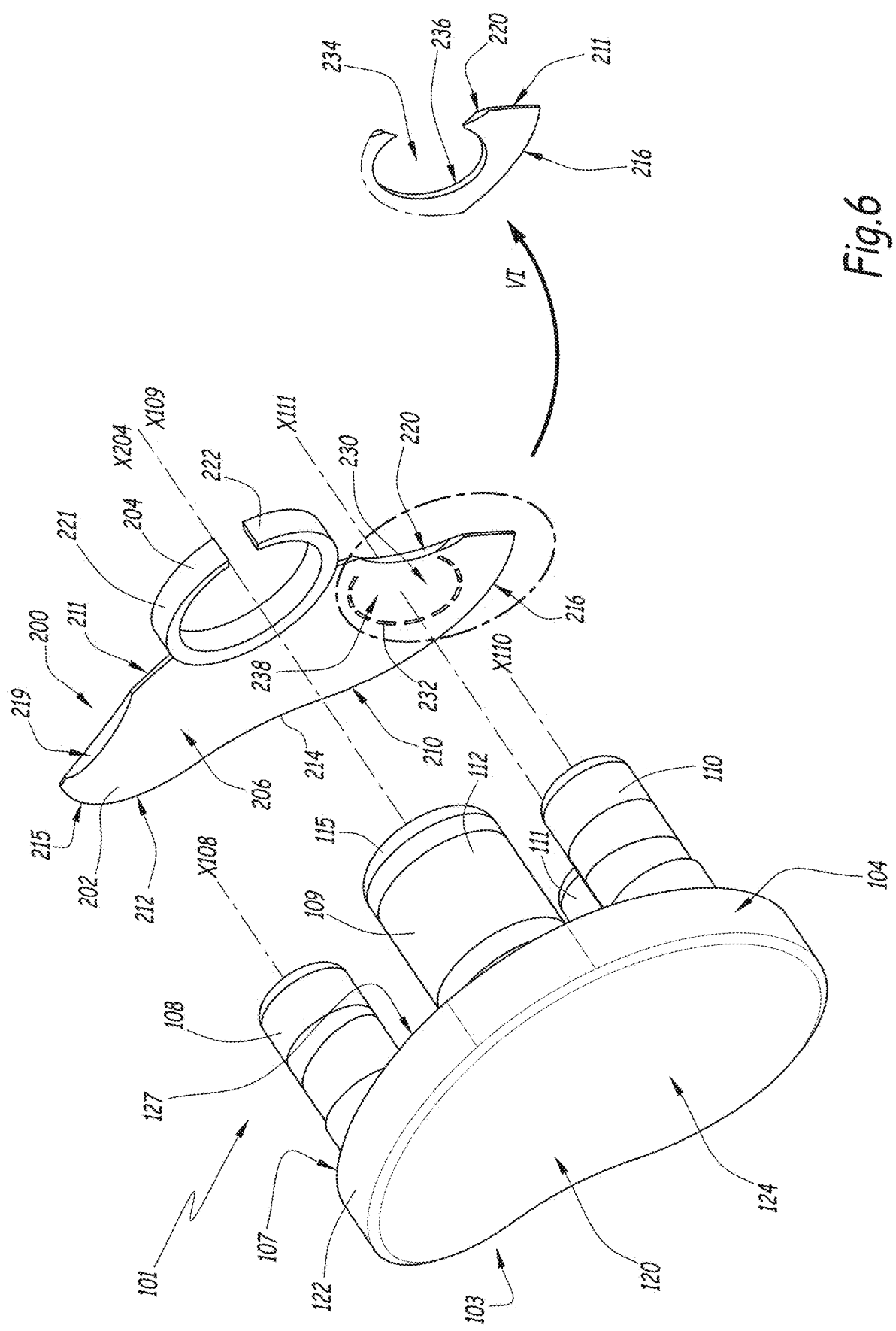
FIGS. 6 and 7 are exploded perspective views of a shoulder prosthesis according a second embodiment of the invention.

As best visible on FIG. 6, the body 202 of the augment insert 200 comprises a breakable portion 230 configured to be broken off the body 202 for making the augment insert 200 shape-compatible with the glenoid component 3 and/or with the glenoid component 103. In other words, the breakable portion 230 may be detached and removed from the body 202 by splitting a portion from said body 202.

The breakable portion 230 is a part of the body 202 and extends from the surface of side 206 to the surface of side 208, in other words throughout the body 202. In other embodiments, the breakable portion may be interior to any peripheral edges.

When the breakable portion 230 is broken off the body 202, an aperture 234 is opened through the body 202, as shown on detail VI of FIG. 6. This aperture 234 extends from the side 206 to the side 208, in other words is formed throughout the body 202. The aperture 234 has a similar shape than the broken off breakable portion 230.

The breakable portion 230 is configured to be manually breakable, or preferably breakable with a non-powered hand-held ancillary, not illustrated. A powered hand-held ancillary may be used instead. By "ancillary", it may be understood "surgical instrument". Alternatively, the breakable portion 230 may be configured not to be manually breakable and to require a non-powered hand-held ancillary or a powered hand-held ancillary, for safety reasons, or for more reliable fixation of the breakable portion 230 should the augment insert 200 be used with the breakable portion 230 left unbroken.

Preferably, the body 202 comprises a pre-cut outline 232 provided throughout the body 202 from the side 206 to the side 208. The pre-cut outline 232 enables manual break-off, or break-off with the aforementioned ancillary. The pre-cut outline 232 delimits the breakable portion 230 when said breakable portion 230 is not broken. The pre-cut outline 232 forms an aperture edge 236 of the aperture 234 when the breakable portion 230 is broken off the body 202.

Other means than the pre-cut outline 232 of the present example may be provided for securing in a breakable manner the breakable portion 230 to the body 202, and may include one or more of the following elements provided in the body 202: breakable leg, fracture initiation zone, notch or portion of lesser thickness.

In the present example, the breakable portion 230 is essentially shaped as a disc, or more precisely as a portion of disc. Thus, the pre-cut outline 232 is shaped as a circle, or a portion of circle. In general, the pre-cut outline 232 extends around the periphery of the breakable portion 230. More generally, the aperture 234 provides free space for accommodating the engaging member 110 of the glenoid component 103, so that said engaging member 111 may extend through the augment insert 200. Consequently, any shape may be chosen for the breakable portion 230 and for the aperture 234 as long as it allows the engaging member 111 to pass through the body 202 so that it can engage the scapula. Preferably, the shape of the breakable portion 230 and of the aperture 234 is chosen to correspond to, or even to coincide with, the shape of the outer peripheral surface of the engaging member 111.

As a consequence, the augment insert 200 may be secured to the glenoid component 103 only if the breakable portion 230 has been broken off. In other words, if the breakable portion 230 is broken off, the augment insert 200 becomes shape-compatible with the glenoid component 103, since the augment insert 200 can be correctly secured to the glenoid component 103, namely in the orientation and position defined above, including the engaging member 111 accommodated through the aperture 234. "Correctly secured" is illustrated on FIGS. 3, 4, 8 and 9, and includes that the side 206 bears against the scapular side of the concerned glenoid component and that the coupling member 204 is secured to the engaging member as described above. If the breakable portion 230 is not broken off, the augment insert 200 is shape-incompatible with the glenoid component 103, namely cannot be correctly secured to the glenoid component 103. The reason is that the engaging member 111 mechanically opposes securing the augment insert 200, which has an incorrect, non-corresponding shape.

The breakable portion 230 may be configured to be broken off by manually pressing said portion 230 onto the engaging member 111.

When the augment insert 200 is assembled onto the side 107, the aperture 234 is coaxial with the axis X111.

In the present example, the location of the engaging member 111 on the side 107 imposes that the breakable portion 230 is provided at the radial edge portion 211. In other words, the breakable portion 230 extends from the radial edge portion 211. More precisely, in the present case, the breakable portion 230 is provided at the cut-away portion 220, namely extends from the cut-away portion 220. When the breakable portion 230 is not broken off, a part of the outline of the cut-away portion 220 is formed by the breakable portion 230.

Depending on the location of the engaging member 111 relative to the side 107, the location of the breakable portion 230 on the body 202 may be modified accordingly. For example, the breakable portion 230 may be provided in a more central location of the body 202, namely inside the peripheral edge 210. The breakable portion 230 may alternatively be provided at the labrum edge portion 212. Locating the breakable portion 230 at the peripheral edge 210 enables an easier manual breaking off, or with the aforementioned ancillary.

Should the breakable portion 230 be broken-off or not, the augment insert 200 of the present example is shape-compatible with the scapular side 7 of the glenoid component 3. However, it is preferred that the breakable portion 230 is not broken off when the augment insert 200 is secured to the glenoid component 3, for a better mechanical stability of the augment insert 200, for a better behavior and/or resistance of the body 202 and advantageously for ensuring a reliable anti-rotation function of the cut-away portion 220, said cut-away portion 220 being fully delimited when the portion 230 is not broken off.

For the augment insert 200 to be shape-compatible with the glenoid component 3 with the breakable portion 230 left unbroken, the breakable portion 230 preferably has a surface 238, which extends at the side 206 of the body 202, when the breakable portion 230 is not broken off, and which is shaped to match the surface 27 of the glenoid component 3 when the side 206 bears against said scapular side 7. In other words, the surface 238 extends continuously to the surface of the side 206.

A surface 240 of the breakable portion 230 at the side 208, namely opposed to the surface 238, preferably extends continuously with the surface of the body 202 on side 208. As a result, when the breakable portion 230 is not broken, side 208 may regularly bear against the scapula 5.

Depending on the number and the location of the engaging members of the glenoid components 3 and 103, or if other shape differences exist for the respective scapular sides of the glenoid components, more than one breakable portion similar to the breakable portion 230 may be provided for the body 202 accordingly.

As visible on FIGS. 6, 9 and 10, the articular side 120 of the glenoid component 103 may comprise a concave articular surface 124, formed integral with the body 122. The surface 124 is configured to cooperate with a convex articular surface provided at a humeral head of the patient in relation with the scapula 105. The surface 124 is preferably of spherical shape, but may have any other suitable convex shape. Said convex articular surface is preferably provided on an artificial humeral head belonging to the prosthesis 101. The concave and the convex articular surfaces together form an artificial joint for the patient, around which the humerus of the patient and the scapula 105 are articulated. The glenoid component 103 having such a concave articular surface 124, the prosthesis 101 and the glenoid component 103 may be qualified of "anatomic".

The geometric center of the concave articular surface 124 is preferably centered on the axis X109.

Instead of being integral with the body 122, the surface 124 may be provided on a part separate from the body 122 and assembled therewith. Instead of a concave articular surface, a convex articular surface may be provided In the present example, the body 122 is made of a single part. Preferably, the body 122 is integral with the engaging members 108, 109, 110 and 111. Alternatively, the body 122 may be made of a plurality of parts of different materials. In this case, the engaging members 108, 109, 110 and 111 may be made of a different material than all or part of the body 122.

The glenoid component 103 is preferably made of a thermoplastic material such as polyethylene. Any other suitable material, such as a metallic material, may be used instead. In an embodiment, at least a part of the glenoid component 103 including the engaging members 108, 109, 110 and 111 and the scapular side 107 may have a lattice structure.

The prosthesis 1 and/or 101 may be provided as a kit, including:
the augment insert 200, with the breakable portion 230 left unbroken,
optionally augment inserts with similar features than the augment insert 200, but with a body of different shape, for example of different thickness or providing a different coverage of the scapular side, such as an augment insert 300 described below,
preferably one or both of the glenoid component 3 and 103,
optionally a humeral head component, and
optionally one or more hand-held ancillary for breaking off the breakable portion 230.

A kit may be provided for a left prosthesis, or for a right prosthesis, or including both prosthesis.

Figure 12:
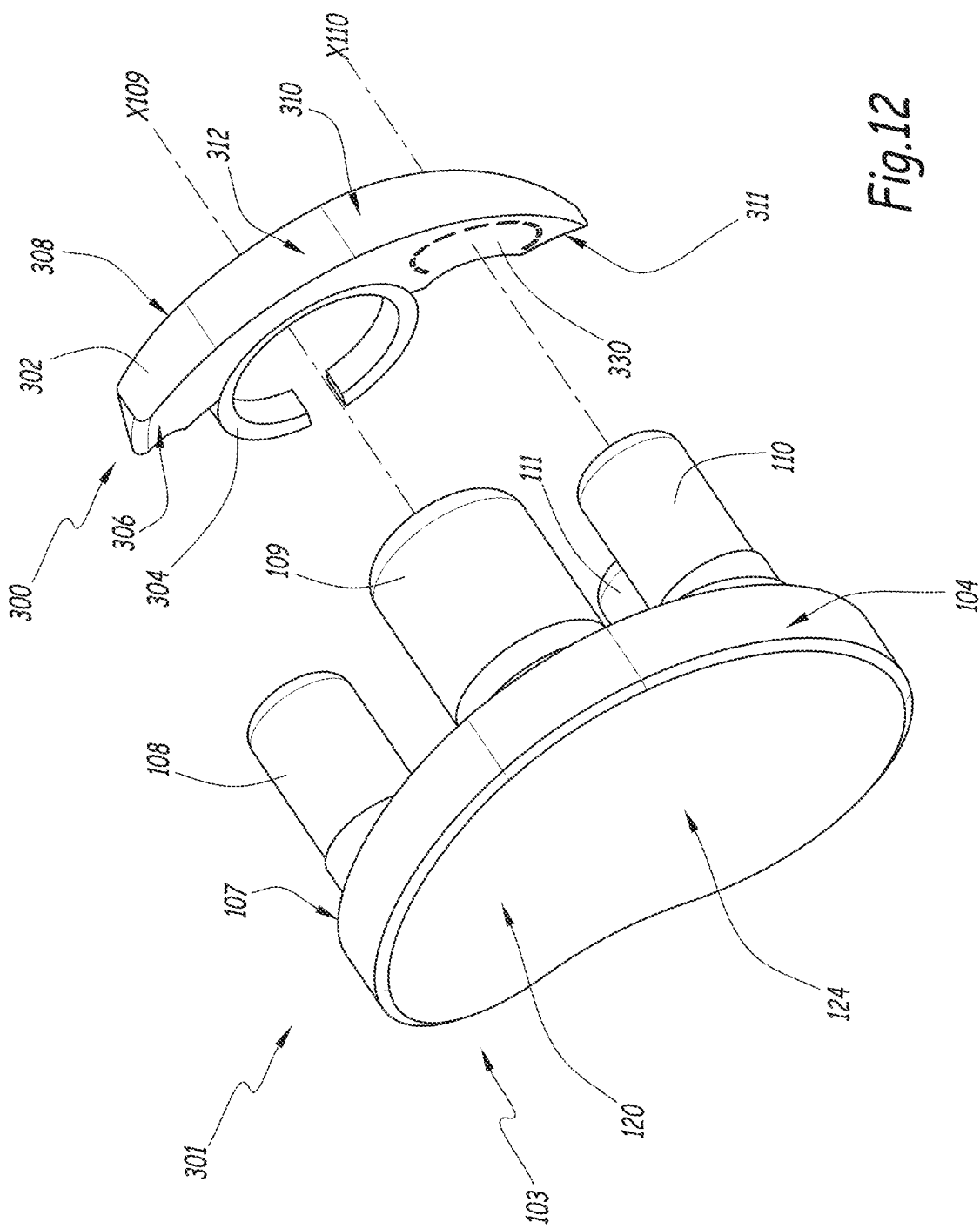
FIG. 12 is an exploded perspective view of a shoulder prosthesis according to a third embodiment of the invention.
Figure 13:
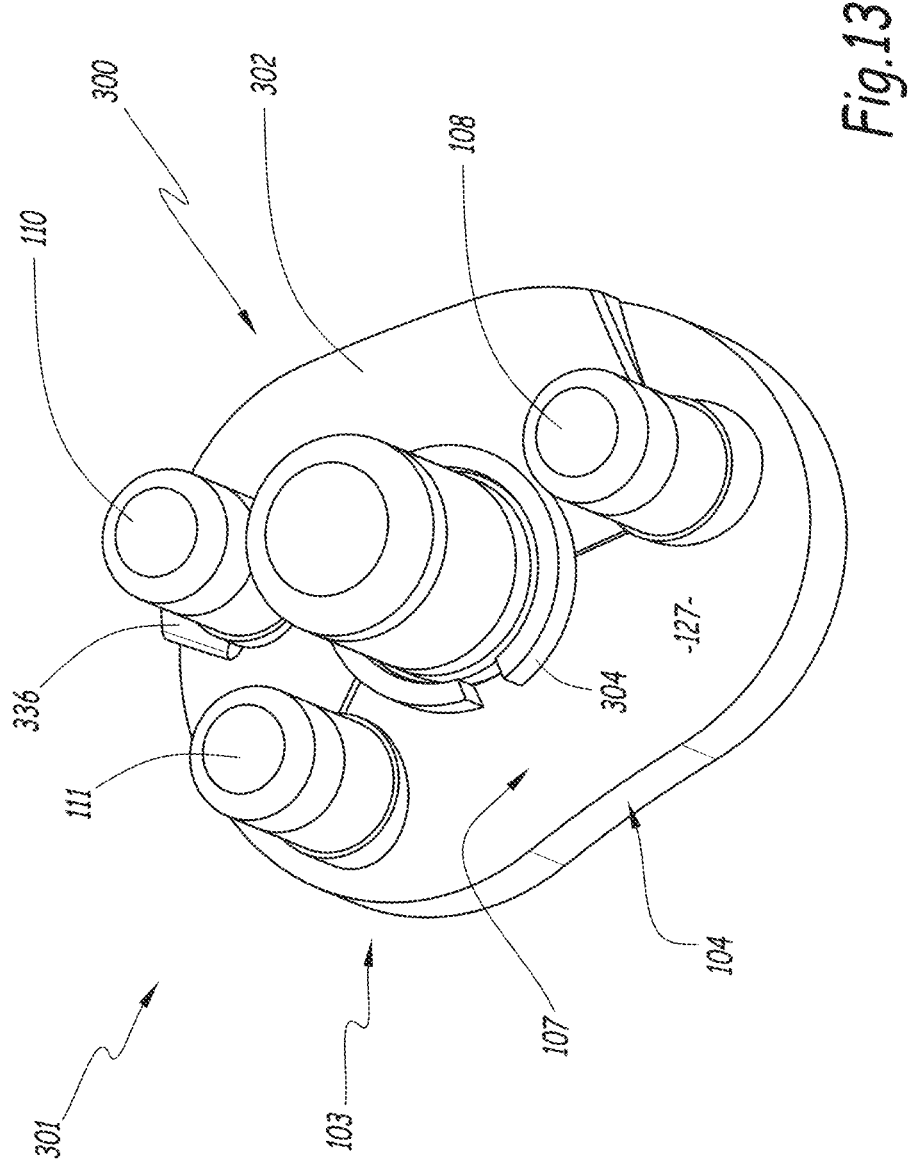
FIG. 13 is an assembled perspective view of the shoulder prosthesis of FIG. 12.
Figure 14:
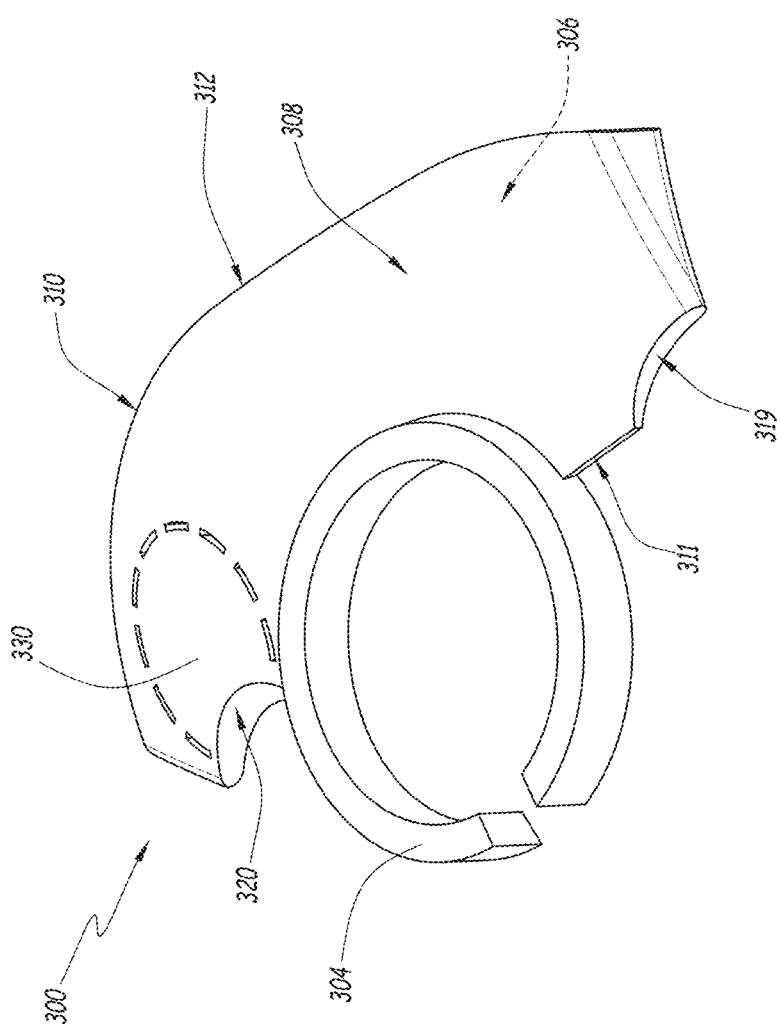
FIG. 14 is a perspective view of an augment insert belonging to the shoulder prosthesis of FIGS. 12 and 13.

Turning now to FIGS. 12 and 13, the glenoid component 103 is illustrated with another embodiment of an augment insert 300, illustrated alone on FIG. 14. The glenoid component 103 and the augment insert 300 belong to a prosthesis 301.

The augment insert 300 has similar features than the augment insert 200, designated with the same terms and/or indicated with similar reference signs augmented of 100. The main differences between the augment insert 300 and augment insert 200 are explicitly described below.

The augment insert 300 mainly comprises a body 302 and a coupling member 304. The body 302 has two opposed sides 306 and 308, a peripheral edge 310 with a radial edge portion 311 and a labrum edge portion 312, cut-away portions 319 and 320 and a breakable portion 330.

The body 302 differs of the body 202 in that said body 302 is shaped to cover a different portion of the scapular side 7 and 107 when the augment insert 300 is secured to the corresponding glenoid component 3 or 103. More precisely, an anterior portion of side 7 or 107 is covered, while a posterior portion of side 7 or 107 is left uncovered. Also, the body 302 covers a portion of smaller area than the body 202, since the body 302 has smaller dimensions. The labrum edge portion 312, alike the labrum edge portion 212, is put in correspondence with a portion of the edge 4 and 104 when the insert 300 is secured respectively to the glenoid component 3 and 103.

Since the body 302 covers a different portion of the scapular sides 7 and 107, the cut-away portion 319 is left free when the augment insert 300 is secured to the glenoid component 3 and accommodates the engaging member 108 when secured to the glenoid component 103, as best visible on FIG. 13. The cut-away portion 320 accommodates engaging member 10 when the augment insert 300 is secured to the glenoid component 3 and the breakable portion 330 is left unbroken. When the augment insert 300 is secured to the glenoid component 103, the breakable portion is broken off and an aperture 336 opened by said braking off accommodates the engaging member 110, as may be best seen on FIG. 13.

Although the described examples apply to human patients, the invention may also be implemented for animal patients.

The invention claimed is:

1. An augment insert, comprising:
 a coupling member for securing the augment insert to a glenoid component of a shoulder prosthesis, and
 a body, comprising:
  a first side, configured to bear against a scapular side of the glenoid component when the augment insert is secured to the glenoid component by means of the coupling member;
  a second side, opposed to the first side and configured to bear against or be adjacent to a scapula of a patient; and
  at least one breakable portion, extending from the first side to the second side and configured to be broken off the body,
 wherein when the breakable portion is broken off the body, an aperture is opened through the body, said aperture extending from the first side to the second side.

2. The augment insert according to claim 1, wherein the aperture is provided for accommodating an engaging member of the glenoid component, said engaging member protruding from a scapular surface of the scapular side of the glenoid component and being configured for securing the shoulder prosthesis to the scapula.

3. The augment insert according to claim 1, wherein the body comprises a pre-cut outline, the pre-cut outline delimiting the breakable portion, and forming an aperture edge of the aperture when the breakable portion is broken off the body.

4. The augment insert according to claim 1, wherein:
the body comprises a peripheral edge delimiting the first side and the second side,
the peripheral edge comprises a thinner radial edge portion and a thicker labrum edge portion, and
the breakable portion is provided at the radial edge portion.

5. The augment insert according to claim 1, wherein the augment insert is at least partially made of a material with a lattice structure.

6. The augment insert according to claim 1, wherein the augment insert is made from additive manufacturing.

7. The augment insert according to claim 1, wherein the first side is of smoother surface and the second side is of rougher surface.

8. A shoulder prosthesis, comprising:
an augment insert according to claim 1, and
a glenoid component, comprising a scapular side to which the augment insert is secured by the coupling member of the augment insert.

9. The shoulder prosthesis according to claim 8, wherein the glenoid component comprises an articular side opposed to the scapular side, the articular side having a convex articular surface.

10. The shoulder prosthesis according to claim 8, wherein the glenoid component comprises an articular side opposed to the scapular side, the articular side having a concave articular surface.

11. A kit, comprising:
a first glenoid component, comprising a scapular side,
a second glenoid component, comprising a scapular side which is shaped differently from the scapular side of the first glenoid component,
an augment insert according to claim 1, the augment insert being:
shape-compatible for bearing against the scapular side of the first glenoid component and shape-incompatible for bearing against the scapular side of the second glenoid component, when the breakable portion is not broken off the body, and
shape-compatible for bearing against the scapular side of the second glenoid component, when the breakable portion is broken off the body.

12. The kit according to claim 11, wherein
the breakable portion has a surface, which extends at the first side of the body when the breakable portion is not broken off, and which is shaped to match a scapular surface of the scapular side of the first glenoid component when the first side bears against said scapular side, and
when the breakable portion is broken off the body, an aperture is opened through the body, said aperture extending from the first side to the second side, the aperture being positioned for accommodating a first engaging member of the scapular side of the second glenoid component.

13. The kit according to claim 11, wherein:
the scapular side of the first glenoid component comprises a second engaging member,
the scapular side of the second glenoid component comprises a third engaging member,
the coupling member of the augment insert is configured for securing indifferently:
the second engaging member, when the first side bears against the scapular side of the first glenoid component, and
the third engaging member, when the first side bears against the scapular side of the second glenoid component.

14. The kit according to claim 11, wherein:
the scapular side of the first glenoid component comprises a fourth engaging member,
the scapular side of the second glenoid component comprises a fifth engaging member, and
the body being provided with a first through-opening or first cut-away portion for accommodating the fourth engaging member when the first side bears against the scapular side of the first glenoid component and a second through-opening or second cut-away portion for accommodating the fifth engaging member when the first side bears against the scapular side of the second glenoid component.

15. The kit according to claim 11, wherein:
the first glenoid component comprises an articular side opposed to the scapular side and comprising a convex articular surface, and
the second glenoid component comprises an articular side opposed to the scapular side and comprising a concave articular surface.

\* \* \* \* \*